(12) United States Patent
Lucht et al.

(10) Patent No.: US 6,982,426 B1
(45) Date of Patent: Jan. 3, 2006

(54) NITRIC OXIDE SENSOR AND METHOD

(75) Inventors: Robert P. Lucht, West Lafayette, IN (US); Thomas N. Anderson, West Lafayette, IN (US); Sherif F. Hanna, College Station, TX (US); Rodolfo Barron-Jimenez, College Station, TX (US); Thomas Walther, Darmstadt (DE); Sukesh Roy, Dayton, OH (US); Michael S. Brown, Dayton, OH (US); James R. Gord, Dayton, OH (US); Jerald A. Caton, College Station, TX (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 23 days.

(21) Appl. No.: 10/914,782

(22) Filed: Aug. 6, 2004

Related U.S. Application Data

(60) Provisional application No. 60/493,564, filed on Aug. 7, 2003.

(51) Int. Cl.
*G01J 1/42* (2006.01)
(52) U.S. Cl. .................................................. 250/373
(58) Field of Classification Search ............. 250/336.1, 250/372, 373
See application file for complete search history.

(56) References Cited

U.S. PATENT DOCUMENTS 6,635,415 B1 * 10/2003 Bollinger et al. .............. 435/4

OTHER PUBLICATIONS

U.S. Provisional Appl. No. 60/493,564, filed Aug. 7, 2003, entitled Diode-Laser-Based Ultraviolet Absorption Sensor for Nitric Oxide.

"Diode Laser Based Sum Frequency Generation of Tunable Wavelength Modulated UV Light for OH Radical Detection", by Daniel B. Oh, Optics Letters, vol. 20, No. 1, Jan. 1, 1995.

(Continued)

*Primary Examiner*—Constantine Hannaher
*Assistant Examiner*—Marcus Taningco
(74) *Attorney, Agent, or Firm*—AFMCLO/JAZ; Richard A. Lambert

(57) ABSTRACT

A nitric oxide sensor and method is disclosed. The sensor is based on sum-frequency mixing of a tunable, 395-nm external cavity diode laser with a 532-nm diode-pumped intracavity-frequency-doubled Nd:YAG laser in a beta-bariumborate crystal. The output from the BBO crystal is ultraviolet radiation at 227 nm and is split using a 50—50 beam splitter. Half of the radiation is directed into a reference photomultiplier tube, and the other half of the UV radiation is directed through the medium of interest and then directed into a signal photomultiplier tube. The output from the photomultiplier tubes is compared and the difference utilized to indicate the level of nitric oxide by absorption-based spectrosocpic techniques.

2 Claims, 1 Drawing Sheet

OTHER PUBLICATIONS

"Development of A Narrow-Band, Tunable, Frequency-Quadrupled Diode Laser for UV Absorption Spectroscopy", by Koplow et al, Applied Optics, vol. 37, No. 18, Jun. 20, 1998.

"High-Sensitivity Detection of CH Radicals in Flames by Use of a Diode-Laser-Based Near-Ultraviolet Light Source", by Peterson et al., Optics Letters, vol. 24, No. 10, May 15, 1999.

"Sum-Frequency Generation With a Blue Diode Laser for Mercury Spectroscopy at 254 nm", by Alnis et al., Applied Physics Letters, vol. 76, No. 10, Mar. 6, 2000.

"OH Detection by Absorption of Frequency-Doubled Diode Laser Radiation at 308 nm", by Barry et al., Chemical Physics Letters 319, Mar. 19, 2000.

"OH Sensor Based on Ultraviolet, Continuous-Wave Absorption Spectroscopy Utilizing a Frequency-Quadrupled, Fiber-Amplified External-Cavity Diode Laser" by Ray et al., Optics Letters, vol. 26, No. 23, Dec. 1, 2001.

"Sum Frequency Generation at 309 nm Using a Violet and a Near-IR DFB Diode Laser for Detection of OH", by Corner et al., Applied Physics B Lasers and Optics 74, Mar. 14, 2002.

* cited by examiner

NITRIC OXIDE SENSOR AND METHOD

CROSS REFERENCE TO RELATED APPLICATIONS

The present application is related to and claims priority on prior copending Provisional Application No. 60/493,564, filed Aug. 7, 2003, entitled Diode-Laser-Based Ultraviolet Absorption Sensor for Nitric Oxide, the entire contents of which are incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to remote sensing equipment and more specifically to a diode laser based nitric oxide sensor.

Nitric oxide (NO) is an atmospheric pollutant that plays a major role in the production of smog. While efforts at reducing pollution have achieved success, the NO output from gas-turbine engines remains high. Because of this, environmental regulations pertaining to NO emissions are becoming increasingly strict. For example, advanced gas turbine engines exhibiting dramatically lower (less than 10 ppm) NO emissions are now available. Currently this 10-ppm level represents the lower detection level of the available NO sensing equipment. NO levels below 10 ppm cannot be accurately measured by existing equipment.

The prior art NO sensing equipment operates based on the absorption of infrared radiation. While somewhat successful, these prior art NO sensors are limited by interferences from water vapor, CO and $CO_2$. Moreover, line strengths are also relatively weak in the infrared region of the spectrum.

A need exists therefore for an improved NO sensor and method providing accurate NO sensing at levels below 10 ppm. Such a sensor would be relatively simple, reliable and low cost. Such a sensor would desirably operate in the ultraviolet spectrum because few molecules absorb in this region, eliminating most interferences.

SUMMARY OF THE INVENTION

Accordingly, it is a primary object of the present invention to provide a NO sensor and method overcoming the limitations of the prior art.

Another object of the present invention is to provide a NO sensor and method capable of accurately determining NO levels below 10 ppm.

Yet another object of the present invention is to provide a NO sensor and method utilizing a diode laser for ultraviolet absorption measurements of NO.

These and other objects of the invention will become apparent as the description of the representative embodiments proceeds.

The operation of the NO sensor of the present invention is based on sum-frequency mixing of a tunable, 395-nm external cavity diode laser (ECDL) with a 532-nm diode-pumped intracavity-frequency-doubled Nd:YAG laser in a beta-barium-borate (BBO) crystal. The output from the BBO crystal is ultraviolet radiation at 227 nm.

After leaving the BBO crystal, half of the UV radiation is directed into a reference photomultiplier tube using a 50—50 beam splitter. The other half of the UV radiation is directed through the medium of interest and then directed into a signal photomultiplier tube. The output from the photomultiplier tubes is compared, and the difference indicates the level of NO by absorption-based spectroscopic techniques. The ECDL is tuned above and below a wavelength of 395.4 so that the sum-frequency-mixed radiation is in resonance with a group of NO lines near 226.87 nm. In this way absorption spectra are created from which the level of NO can be determined by standard spectroscopic techniques. This calculation is readily made by a dedicated microprocessor.

BRIEF DESCRIPTION OF THE DRAWING

The accompanying drawing, incorporated in and forming a part of the specification, illustrates several aspects of the present invention and together with the description serves to explain the principles of the invention. In the drawing.

DETAILED DESCRIPTION OF THE INVENTION

Figure 1:
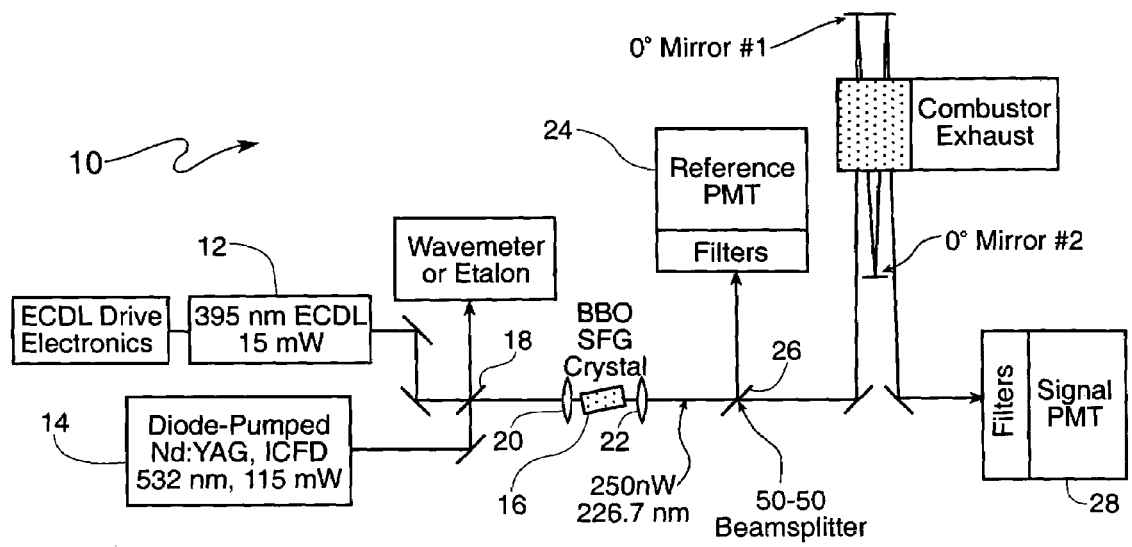
FIG. 1 is a schematic representation of the nitric oxide sensor of the present invention.

Reference is made to FIG. 1 showing the system 10 of the present invention. As will be described in detail below, the method of sensing nitric oxide of the present invention advantageously determines the level of nitric oxide (NO) contained within a medium of interest at levels of 10 ppm or less, thereby exhibiting far greater sensitivity than the prior art systems and methods.

The nitric oxide sensor and method of the present invention is based on ultraviolet absorption measurements of the NO molecule and is based on sum-frequency mixing of the output of a tunable, 395-nm external cavity diode laser (ECDL) 12 and a 532-nm diode pumped, frequency-doubled Nd:YAG laser 14 in a beta-barium-borate (BBO) crystal 16. The ECDL 12 beam and the Nd:YAG laser 14 beam are overlapped by a dichroic mirror 18 prior to admission into the BBO crystal 16. The output from the BBO crystal 16 is ultraviolet radiation at 226.8 nm, corresponding to the (v'=0, v"=0) band of the $A^2\Sigma^+ - X^2\Pi$ electronic transition of NO. A focusing lens 20 is provided ahead of the BBO crystal 16 and a collimating lens 22 is provided after the BBO crystal 16. A wavemeter or etalon is provided to monitor the ECDL 12 output.

After leaving the BBO crystal 16, a reference beam equaling half of the UV radiation is directed into a reference photomultiplier tube 24 using a 50—50 beam splitter 26. The other half of the UV radiation in the form of a signal beam is directed through the medium of interest. Advantageously, the simultaneous detection of the reference beams and signal beams allows the subtraction of common-mode noise and etalon effects at the crystal surfaces and significantly enhances detection efficiency.

As shown in FIG. 1, the medium of interest is a combustor exhaust stream. The signal beam, after passing through the medium of interest is directed into a signal photomultiplier tube 98. As shown, one or more mirrors may be used to direct the signal beam through the medium of interest, depending on the physical layout of the sensor. As also shown in FIG. 1, the photomultiplier tubes 24, 28 include interference filters to filter the 532-nm and 395-nm beams as well as any flame emission. Additionally, metallic neutral density filters are used to attenuate both beams to keep the photomultiplier tubes 24, 28 from saturating and maintain linearity of the detectors.

The output from the photomultiplier tubes 24, 28 is compared, and the difference indicates the level of NO by absorption-based spectroscopic analysis. During operation, the ECDL 12 is tuned above and below a wavelength of 395.4 nm so that the sum-frequency-mixed radiation is in resonance with a group of NO lines near 226.87 nm. In this way absorption spectra are created from which the level of NO can be determined by conventional spectroscopic techniques. The calculation assumes a Voight profile with a Doppler width (full width half maximum) of 2.97 GHz and is readily made by a dedicated microprocessor, not shown.

Figure 2:
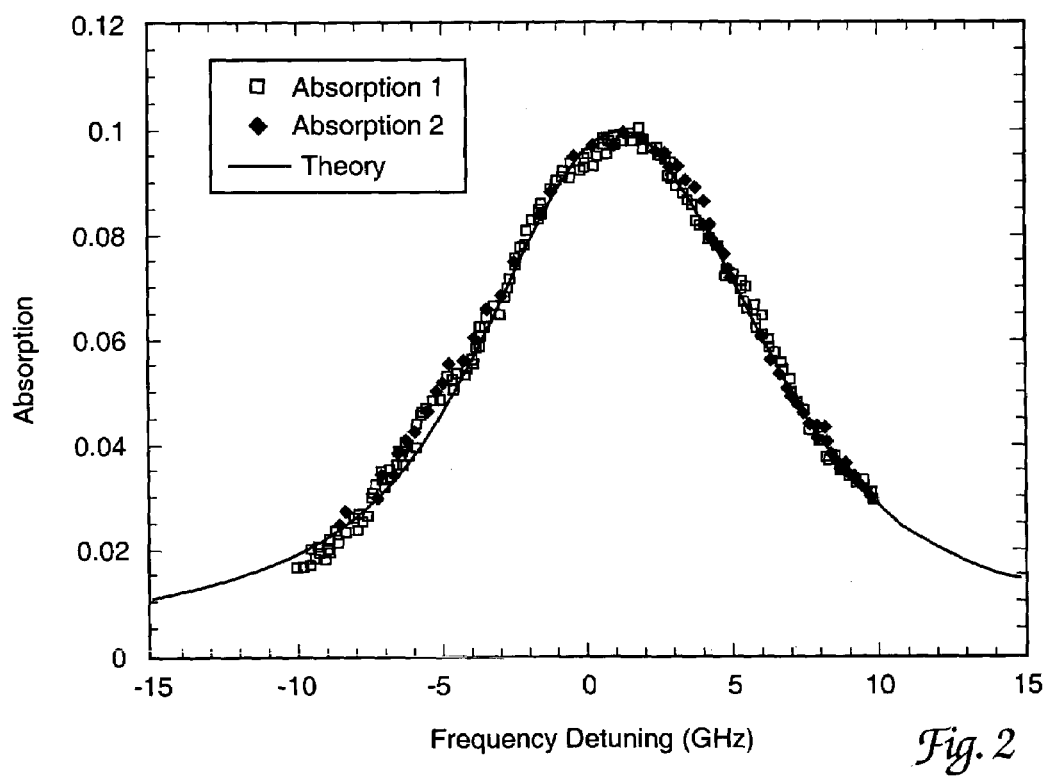
FIG. 2 is a graph illustrating the NO levels obtained by use of the nitric oxide sensor and method of the present invention versus a theoretical curve.

As an example of the method of the present invention, field tests were conducted analyzing the exhaust stream from a liquid-fueled gas turbine auxiliary power unit. To aid in processing the data, the temperature of the exhaust gasses was measured at the location of the signal beam using thermocouples. The center frequency of the ECDL 12 was tuned to 395.237 nm to produce an ultraviolet output from the BBO crystal 16 of 226.87 nm, which is in resonance with the $P_2(10)$ and $^FQ_{12}(10)$ overlapped transitions at 44087.70 cm$^{-1}$ and 44087.77 cm$^{-1}$, respectively. This line was chosen because it is less sensitive to temperature and is isolated enough to scan the peak and the baseline in one scan, even at atmospheric pressures. FIG. 2 is a graph showing the results from this test conducted at high load. As shown, the measured absorption values track the theoretical values with a high degree of accuracy. The agreement between the experimental and theoretical line shapes in FIG. 2 along with an observed excellent agreement between the theoretical parameters and measured values indicate that the nitric oxide sensor of the present invention is capable of operating accurately despite the extreme noise and vibrations in an actual combustion environment. The sensitivity of the sensor of the present invention was determined to correspond to a detection limit of 0.2 ppm per meter path length at 300 K or 0.6 ppm per meter path length at 1000 K gas.

In summary, numerous benefits have been described from utilizing the principles of the present invention. The present invention provides a nitric oxide sensor and method providing high accuracy and sensitivity. The sensor utilizes the technique of sum-frequency mixing of two solid state lasers to produce a UV beam, that is split with one half being sent to a reference photomultiplier tube and the other half being passed through the medium of interest and then received by a signal photomultiplier tube. The output from the photomultiplier tubes is compared, and the difference indicates the level of nitric oxide by absorption-based spectroscopic techniques. In this way, accurate, reliable NO measurements at very low levels are possible.

The foregoing description of the preferred embodiment has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the inventions in various embodiments and with various modifications as are suited to the particular scope of the invention as determined by the appended claims when interpreted in accordance with the breadth to which they are fairly, legally and equitably entitled.

What is claimed is:

1. A nitric oxide sensor, comprising:
   a 532-nm diode pumped intracavity frequency doubled Nd:YAG laser;
   a 395-nm external cavity diode laser including driver electronics;
   a dichroic mirror for overlapping the output of said external cavity diode laser and said Nd:YAG laser;
   a beta-barium-borate crystal including a focusing lens ahead of said crystal and a collimating lens after said crystal, said crystal being positioned to receive the output from said dichroic mirror and to generate a sum-frequency-mixed radiation beam at 227 nm;
   a 50—50 beam splitter for splitting said radiation beam from said beta-barium-borate crystal into a reference beam and a signal beam;
   a reference photomultiplier tube for generating a reference output from said reference beam;
   at least one mirror for passing said signal beam through a medium of interest;
   a signal photomultiplier tube for generating a signal output from said signal beam; said signal photomultiplier tube receiving said signal beam after passage through the medium of interest; and,
   a microprocessor for comparing said signal output and said reference output to determine the level of nitric oxide within the medium of interest.

2. A method of sensing nitric oxide within a test medium, comprising the steps of:
   providing a 532-nm diode pumped intracavity frequency doubled Nd:YAG laser;
   providing a tunable 395-nm external cavity diode laser;
   overlapping the output of said external cavity diode laser and said Nd:YAG laser by use of a dichroic mirror;
   generating a sum-frequency-mixed radiation beam at 227 nm from the result of said overlapping step above by use of a beta-barium-borate crystal including a focusing lens ahead of said crystal and a collimating lens after said crystal;
   tuning said ECDL above and below 395.4 nm so that said sum-frequency-mixed radiation is in resonance with the group of NO lines near 226.87 nm;
   splitting said radiation beam from said beta-barium-borate crystal into a reference beam and a signal beam using a 50—50 beam splitter;
   providing a reference photomultiplier tube for generating a reference output corresponding to said reference beam;
   passing said signal beam through the medium of interest;
   providing a signal photomultiplier tube for generating a signal output corresponding to said signal beam after its passage through the medium of interest;
   comparing said signal output and said reference output; and,
   determining the level of nitric oxide within the medium of interest.

\* \* \* \* \*